United States Patent [19]

Lambur

[11] Patent Number: 5,438,706
[45] Date of Patent: Aug. 8, 1995

[54] LATERAL EYE SHIELDING DEVICE

[76] Inventor: James A. K. Lambur, 7600 W. College Dr., Palos Heights, Ill. 60463

[21] Appl. No.: 218,067

[22] Filed: Mar. 25, 1994

[51] Int. Cl.$^6$ ............................................. A61F 9/04
[52] U.S. Cl. ............................................. 2/13; 2/449
[58] Field of Search .................. 2/449, 448, 451, 13, 2/12, 10, 9, 431, 432, 444; 351/47, 44, 48, 123

[56] References Cited

U.S. PATENT DOCUMENTS

| | | | |
|---|---|---|---|
| 508,457 | 11/1893 | Wickliffe | 351/123 |
| 2,460,373 | 2/1949 | Waldman | 2/12 X |
| 2,643,381 | 6/1953 | Abbott | 2/432 |
| 3,011,170 | 12/1961 | Lutz | 2/13 |
| 3,505,679 | 4/1970 | Bennett | 351/47 X |
| 3,596,290 | 8/1971 | Kennedy | 2/13 |
| 3,721,490 | 3/1973 | Prince | 351/47 |
| 4,349,251 | 9/1982 | Shedrow | 351/47 X |
| 4,682,374 | 7/1987 | Geiser | 351/123 X |

*Primary Examiner*—Peter Nerbun
*Attorney, Agent, or Firm*—Michael R. McKenna

[57] ABSTRACT

A removably attachable eyeglass safety device providing lateral eye shielding comprising a pair of safety shields that have a plurality of vertically spaced independent means for attachment, The user may select one of the means for attachment that positions the safety shield at a height or vertical position relative to the temple arm to provide maximum lateral shielding of the eye for the task against which eye safety is required. The eyeglass safety device fits a variety of select sized temple arms,

3 Claims, 1 Drawing Sheet

U.S. Patent　　　　Aug. 8, 1995　　　　5,438,706
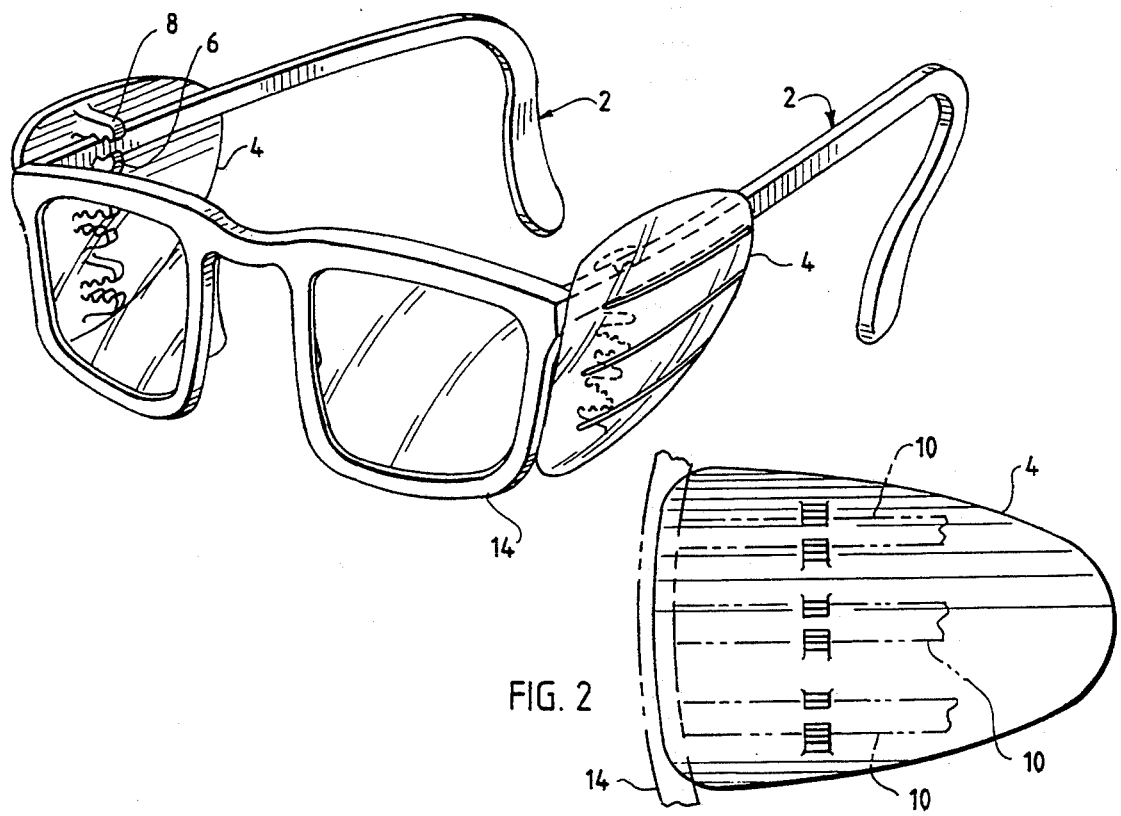
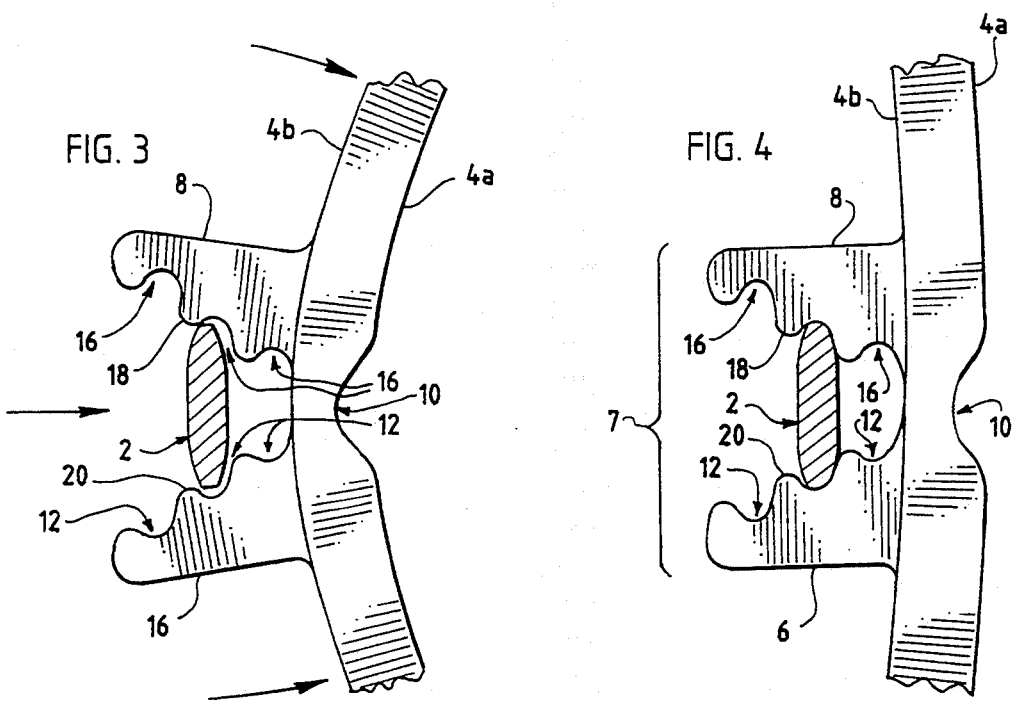

LATERAL EYE SHIELDING DEVICE

BACKGROUND OF THE INVENTION

This invention relates to a safety device for protecting the human eye. In particular, it relates to a lateral eye shielding device which may be removably attached to and supported by the temple arm of conventional eyeglass frames. It may be adjusted vertically relative to the temple arm, to shield the eye from infectious splatter, which may arise in the course of an operative procedure.

Various modes of lateral eye protection are known in the prior art. See for example U.S. Pat. No. 4,298,991, for peripheral view finders, which discloses an apparatus to limit the peripheral vision of the user, with lateral shields which pivotally attach to the temple arms and where pivotal movement is restricted so that the shields can be placed in one of two positions, to either block the peripheral vision or to leave it unobstructed.

See also U.S. Pat. No. 4,105,304 for a side glare eliminating device, which attaches at the temple arm of the eyeglasses. Each side of the shield member provided has two overlapping shields, one of which is positioned rigidly along the temple member and the other is pivotally moveable to adjust the angular orientation with respect to the temple member to lower the elevation of the shield from a singular overlapping point of attachment.

A variety of other eye protectors which are mounted on eyeglasses, particularly at the temple member thereof, are disclosed in U.S. Pat. Nos. 2,224,784; 3,721,490; 3,505,679; and 2,858,839. None of the foregoing patents disclose a side shield with a plurality of means to allow the shield to be attached at varying elevations relative to the temple member and the eye. Nor do these prior art devices allows the full shield to be positioned at variable elevations relative to the temple arm in order to provide protection from specific sources which are at varying lateral angles from the eye.

Moreover, a principal disadvantage of such known devices is their cost.

ADVANTAGES OF THIS INVENTION

The preferred embodiments of this invention provide improved lateral eye shielding because a plurality of independent vertical jaws positioned at a spaced vertical distance from one another as a means for attaching the shield member to the temple arms allows the user to select the appropriate height or vertical position of the shield member at a distinct vertical position relative to the temple arm which will provide maximum lateral shielding of the eye for the task against which eye safety is sought.

Unlike the foregoing devices which teach structures that can be easily pivoted and moved out of position, the instant invention relates to a temple arm mounted shield that has a plurality of independent means for attachment that allow the shield to be removably positioned in a variety of elevations relative to the temple arm and the eye.

The prior art structures that are movable relative to the eye are permanently affixed to the eyeglass frame, and thus, may not be used on more than one pair of eyeglasses. To alleviate this problem, and others which will become apparent from the disclosure which follows, the present invention conveniently detaches from the temple arm of the eyeglass frame and is adapted to fit a variety of select sized temple members. This device is easily detached by bending the shield member, thus releasing the vertical jaw which has been adapted with ribbets arranged and adapted to accommodate select styles of eyeglass frames having different sized temple members.

It is apparent that the comparable cost of manufacturing the eye shielding safety device taught by this invention will be low due to the ease and simplicity of its design.

Still other advantages will be apparent from the disclosure that follows.

SUMMARY OF THE INVENTION

The invention relates to a lateral eye shielding device, adapted for use with optical glasses having a pair of temple arms. The device comprises a pair of shield members. Each shield member has a plurality of independent means for attaching the shield member to one of the temple arms. Each of the independent means for attaching the shield member to one of the temple arms is positioned at a spaced vertical distance from one another. By selective employment of one of the independent means for attaching the shield member to a temple arm, the shield member may be selectively positioned at distinct vertical positions relative to the temple arm to provide variable vertical positioning of the lateral eye shielding device.

BRIEF DESCRIPTION OF THE DRAWING

Preferred embodiments of the invention are described hereinafter with reference to the accompanying drawing wherein:

FIG. 1 is a perspective view of a preferred embodiment of the invention for a lateral eye shielding device showing each shield member having three independent means for attaching the shield member to a temple arm and showing the uppermost vertical jaw of each shield member attached to a temple arm of the optical glasses to position the shield member in its lowest vertical position;

FIG. 2 is a side fragmentary elevation view of a preferred embodiment of this invention showing the relative position of the shield member to the temple arm of the optical glasses when various vertical jaws of the shield member are employed;

FIG. 3 is a detailed fragmentary cross-sectional view of a preferred embodiment of the lateral eye shielding device of the invention showing the vertical jaw having an upper jaw member and a complementary mirror image lower jaw member, each of said jaw members being independently disposed on the inner surface of the shield member, so when the shield member is flexibly bent (as shown) the upper jaw member and its complementary lower jaw member are separated. Said figure further shows a plurality of rabbets disposed on the lower surface of the upper jaw member and the upper surface of the complementary mirror image lower jaw member where each rabbet is arranged and adapted to accommodate a select sized temple member. Said figure further shows a horizontal surface void disposed on the outer surface of the shield member in positional arrangement with the vertical jaw disposed on the inner surface thereof; and FIG. 4 is a detailed fragmentary cross-sectional view of the preferred embodiment shown in FIG. 3 with the shield member in a static, non-flexed position.

DETAILED DESCRIPTION OF THE INVENTION

The preferred embodiments depicted in the drawing comprise a lateral eye shielding device, adapted for use with optical glasses 14 having a pair of temple arms 2, comprising a pair of shield members 4, each shield member 4 having a plurality of independent means for attaching the shield member to one of the temple arms 2. Each independent means for attaching the shield member 4 to one of the temple arms 2 is positioned at a spaced vertical distance from one another, so that by selective employment of one of the independent means for attaching the shield member to a temple arm, the shield member 4 may be selectively positioned at distinct vertical positions relative to the temple arm as is particularly shown in FIG. 2, whereby variable vertical lateral shielding of the eye is provided.

The preferred embodiments of this invention show an improved lateral eye shielding device for attachment to optical glasses 14 having a pair of temple arms 2 to which lateral shield members 4 may be attached. This device comprises a plurality of independent means for attaching the shield member 4 to one of the temple arms 2. Each of the independent means for attachment is positioned at a spaced vertical distance from one another. Thus, the shield member 4 may be selectively positioned at distinct vertical positions relative to the temple arm 2 to provide variable vertical lateral shielding of the eye by selective employment of one of the independent means for attaching the shield member 4 to one of the temple arms 2.

Without departing from the generality of the invention disclosed herein and without limiting the scope of the invention, the discussion that follows, will refer to the invention as depicted in the drawing.

The preferred embodiments of the apparatus depicted in the drawing comprise a lateral eye shielding device comprising a pair of shield members 4, each shield member having three independent vertical jaws 7 for attaching the shield member 4 to one of the temple arms 2. As best shown in FIG. 1 of the drawing, each vertical jaw 7 is positioned at a spaced vertical distance from one another. By selective employment of one of the independent vertical jaws 7, the shield member 4 may be selectively positioned at three distinct vertical positions relative to the temple arm 2, whereby variable vertical lateral shielding of the eye is provided. In the lateral eye shielding device of the present invention, each shield member 4 has an inner surface 4b and an outer surface 4a and the vertical jaws 7 are disposed on the inner surface 4b.

Each vertical jaw 7 has an upper jaw member 8 and a complementary mirror image lower jaw member 6. The upper jaw member 8 of the vertical jaw 7 has a lower surface 18 in opposition to an upper surface 20 of the complementary mirror image lower jaw member 6. The temple member 2 may be removably secured between the lower surface 18 of the upper jaw member 8 and the upper surface 20 of the complementary mirror image lower jaw member 6.

As shown in FIG. 3, the lateral eye shielding device of the present invention provides that each shield member 4 is flexibly resilient. It is shown that each of said jaw members 6,8 is independently disposed on the inner surface 4b of the shield member 4, so when the shield member is flexibly bent, as shown in FIG. 3, the upper jaw member 8 and its complementary lower jaw member 6 are separated, as compared to vertical jaw 7 of FIG. 4 when the shield member 4 is static.

FIG. 3, further shows three rabbets 16 disposed on the lower surface 18 of the upper jaw member 8 and three rabbets 12 disposed on the upper surface 20 of the complementary mirror image lower jaw member 6. The rabbets of each jaw member are arranged and adapted to accommodate a select sized temple member 2.

A preferred embodiment of the present invention provides a plurality of horizontal surface voids 10. Each horizontal surface void 10 is disposed on the outer surface 4a of the shield member 4 in positional arrangement with one of the vertical jaws 7 disposed on its inner surface 4b.

The upper jaw member 8 and its complementary mirror image lower jaw member 6 of each vertical jaw 7 is each independently disposed on the inner surface 4b of the shield member 4. This independence allows each vertical jaw 7 to be selectively operable between a closed position when the shield member 4 is static and an open position when the shield member is flexibly bent to increase the inner surface 4b. In this way, each upper jaw member 8 and its complementary mirror image lower jaw member 6 may be separated as the vertical jaw 7 is opened to receive or release a temple member 2 which may be arranged therein.

In another preferred embodiment of the present invention, at least one member, either the upper jaw member 8 or its complementary mirror image lower jaw member 6, or both members, are flexibly resilient, so that a temple arm 2 may be resistantly admitted and withdrawn therefrom.

As shown in FIG. 4, a preferred embodiment of the present invention provides that the inner surface 4b of the shield member 4 is concave and the outer surface 4a is convex.

While this invention has been described in connection with the best mode presently contemplated by the inventor for carrying out his invention, the preferred embodiments described and shown are for purposes of illustration only, and are not to be construed as constituting any limitations of the invention. Modifications will be obvious to those skilled in the art, and all modifications that do not depart from the spirit of the invention are intended to be included within the scope of the appended claims.

What I claim is:

1. A lateral eye shielding device, adapted for use with optical glasses having a pair of temple arms, comprising a pair of shield members, each shield member having a plurality of independent means for attaching the shield member to one of the temple arms, each independent means for attaching the shield member to one of the temple arms being positioned at a spaced vertical distance from one another, so that by selective employment of one of the independent means for attaching the shield member to a temple arm, the shield member may be selectively positioned at distinct vertical positions relative to the temple arm, whereby variable vertical lateral shielding of the eye is provided, each shield member has an inner surface and an outer surface and the plurality of independent means for attaching the shield member to one of the temple arms are disposed on the inner surface thereof, and wherein each of the independent means for attaching the shield member to one of the temple arms comprises a vertical jaw having an upper jaw member and a complementary mirror image lower jaw member, said upper jaw member of the vertical jaw has a lower surface in opposition to an upper surface of the complementary mirror image lower jaw member, whereby a temple member may be removably secured therebetween, and wherein the lower surface of the upper jaw member of the vertical jaw and the upper surface of the complementary mirror image lower jaw member each contain a plurality of rabbets for individually gripping a select sized temple member.

2. The lateral eye shielding device of claim 1, wherein at least one member of each vertical jaw is flexibly resilient, so that a temple arm may be resistantly admitted and withdrawn therefrom.

3. A lateral eye shielding device, adapted for use with optical glasses having a pair of temple arms, comprising a pair of flexibly resilient shield members each having an inner concave surface and an outer convex surface, and wherein a. each shield member has a plurality of independent means for attaching the shield member to one of the temple arms, each of which comprises a vertical jaw having an upper jaw member and a complementary mirror image lower jaw member, each independently disposed on the inner concave surface thereof, said upper jaw member of the vertical jaw has a lower surface in opposition to an upper surface of the complementary mirror image lower jaw member, each vertical jaw is selectively operable between a closed position when the shield member is static and an open position when the shield member is flexibly bent toward making the inner concave surface convex, so that when a shield member is flexibly bent toward making the inner concave surface convex the upper jaw member and its complementary mirror image lower jaw member are thereby separated, whereby the vertical jaw is opened to receive or release a temple member which may be arranged therein;

b. the lower surface of the upper jaw member of the vertical jaw and the upper surface of the complementary mirror image lower jaw member each containing a plurality of rabbets for individually gripping a select sized temple member; and c. each vertical jaw being positioned at a spaced upright distance from one another, so that by selectively employing one of the vertical jaws the shield member may be selectively positioned at a different vertical position relative to the temple arm to provide variable vertical lateral shielding of the eye.

* * * * *